US007526954B2

(12) United States Patent
Haselhurst et al.

(10) Patent No.: US 7,526,954 B2
(45) **Date of Patent: *May 5, 2009**

(54) GAIT ASSISTIVE SYSTEM AND METHODS FOR USING SAME

(75) Inventors: Richard S. Haselhurst, Fort Lauderdale, FL (US); Jon R. Christiansen, Hampton, VA (US); Steven M. Willens, Pleasanton, CA (US)

(73) Assignee: Instep USA, LLC, Fort Lauderdale, FL (US)

( * ) Notice: Subject to any disclaimer, the term of this patent is extended or adjusted under 35 U.S.C. 154(b) by 227 days.

This patent is subject to a terminal disclaimer.

(21) Appl. No.: 11/619,049

(22) Filed: Jan. 2, 2007

(65) Prior Publication Data

US 2007/0204687 A1 Sep. 6, 2007

Related U.S. Application Data

(63) Continuation-in-part of application No. 10/897,694, filed on Jul. 24, 2004, now Pat. No. 7,191,644.

(51) Int. Cl.
*A61B 5/00* (2006.01)

(52) U.S. Cl. .................................... 73/172; 73/862.391

(58) Field of Classification Search .................. 73/172, 73/862.391

See application file for complete search history.

(56) References Cited

U.S. PATENT DOCUMENTS

| | | | | |
|---|---|---|---|---|
| 5,323,650 | A * | 6/1994 | Fullen et al. | 73/172 |
| 6,031,463 | A | 2/2000 | Bechmann | |
| 6,033,370 | A * | 3/2000 | Reinbold et al. | 600/595 |
| 6,195,921 | B1 * | 3/2001 | Truong | 36/136 |
| 6,326,539 | B1 | 12/2001 | Mishima | |
| 6,377,178 | B1 | 4/2002 | DeToro et al. | |
| 6,752,028 | B2 | 6/2004 | Bechmann | |
| 6,807,698 | B2 | 10/2004 | Torbet et al. | |
| 6,865,825 | B2 | 3/2005 | Bailey, Sr. et al. | |
| 7,191,644 | B2 * | 3/2007 | Haselhurst et al. | 73/172 |

* cited by examiner

*Primary Examiner*—Max Noori
(74) *Attorney, Agent, or Firm*—Ballard Spahr Andrews & Ingersoll, LLP

(57) ABSTRACT

Systems and methods for providing biofeedback information to a subject for gait assistive therapy are provided. The system comprises an insole pressure sensor and means for communicating the pressure exerted by the subject on the insole pressure sensor to the subject. The insole pressure sensor comprises conductive elements in communication with a transmitter, which transmits a pressure signal to a receiver worn by the subject. The method comprises monitoring pressure applied by the subject to the insole pressure sensor, monitoring a pressure threshold of the insole pressure sensor, and transmitting an output signal when the pressure exceeds a pre-determined pressure threshold. The insole pressure sensor in various aspects has a ball portion and heel portion corresponding to the respective ball and heel of a subject's foot.

24 Claims, 7 Drawing Sheets

GAIT ASSISTIVE SYSTEM AND METHODS FOR USING SAME

CROSS REFERENCE TO RELATED APPLICATIONS

This application is a continuation-in-part of, and claims priority to and the benefit of U.S. patent application Ser. No. 10/897,694, entitled "System Incorporating an Insole Pressure Sensor and Personal Annunciator for Use in Gait Assistive Therapy," filed Jul. 24, 2004, now U.S. Pat. No. 7,191,644 which application is hereby incorporated by this reference in its entirety.

FIELD OF THE INVENTION

This invention relates generally to systems, devices, and methods to assist the gait of a subject, and more particularly to an insole pressure device, and systems and methods therefore, which is configured to monitor and transmit information regarding pressure exerted on an insole pressure sensor to the subject to create an extra neural pathway for use in gait assistive therapy.

BACKGROUND

One of the problems associated with hip, knee and foot surgery is a loss of sensation in the affected limb, particularly in the lower region including the foot. Although the limb may be physically whole and the associated muscles are controllable, confirmation of contact between the foot and the ground is necessary. Typically, a subject needs to rely on visual confirmation of the foot's position. Visual confirmation is also essential in the case of amputation (i.e., where a prosthetic device would be used in combination with the remaining limb), and certain degenerative conditions due to medical or other circumstances, such as diabetes, frostbite and obesity.

Those without sensation in the lower limbs also experience difficulty in performing activities that require vision to be concentrated somewhere other than on the patient's limb or foot. For example, while operating machinery, such as a motor vehicle, vision must be concentrated on the machine in use or its surroundings. Activities such as negotiating steps and ladders, stepping backwards, responding to moving objects (i.e., crossing a road in traffic), walking in darkness or on uneven surfaces, and carrying large objects are made much more difficult without sensory feedback from the feet.

In other circumstances, other medical conditions or treatments may prevent a patient from being able to concentrate visually on the movement of the feet. For example, post-surgical medication given to patients after hip, knee or foot surgery can often reduce a patient's ability to concentrate visually on the feet. Certain medical conditions, such as progressive supranuclear palsy (PSP) and certain balance disorders for example, can also preclude a patient from looking downwards to visually check each step that is taken.

Currently, known devices are limited to measuring pressure within a single, limited portion of the foot, and are limited to use for gait corrective therapy in a clinical environment. Therefore, there is a need in the art for devices that are not limited to sensing pressure in only one portion of the foot and can be used both in and out of a clinical environment to create an extra neural pathway for gait corrective therapy.

SUMMARY OF THE INVENTION

In accordance with the purpose(s) of this invention, as embodied and broadly described herein, this invention, in one aspect, relates to systems for providing biofeedback information to a subject to create an extra neural network for gait assistive therapy. In one aspect, the system comprises an insole pressure sensor and means for communicating the position of at least a portion of a subject's foot relative to the insole pressure sensor to the subject. In a further aspect, the insole pressure sensor comprises a plurality of conductive foam cores, with at least one conductive foam core disposed within a first portion of the insole pressure sensor, and at least one other foam core disposed within a second portion of the insole pressure sensor. In another aspect, the first portion of the insole pressure sensor can be a heel portion and the second portion of the insole pressure sensor can be a ball portion.

In another exemplary aspect, the invention relates to a method of providing biofeedback information to a subject for gait assistive therapy. In one aspect, the method comprises monitoring pressure applied by the subject to at least a portion of an insole pressure sensor, monitoring a pressure threshold for one or more portions of the insole pressure sensor and transmitting an output signal when the pressure in at least one portion of the insole pressure sensor exceeds a pre-determined pressure threshold. In yet another aspect, the insole pressure sensor comprises a ball portion and a heel portion.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention. Like numbers represent like elements throughout the figures.

DESCRIPTION OF THE PREFERRED EMBODIMENTS

Figure 1:
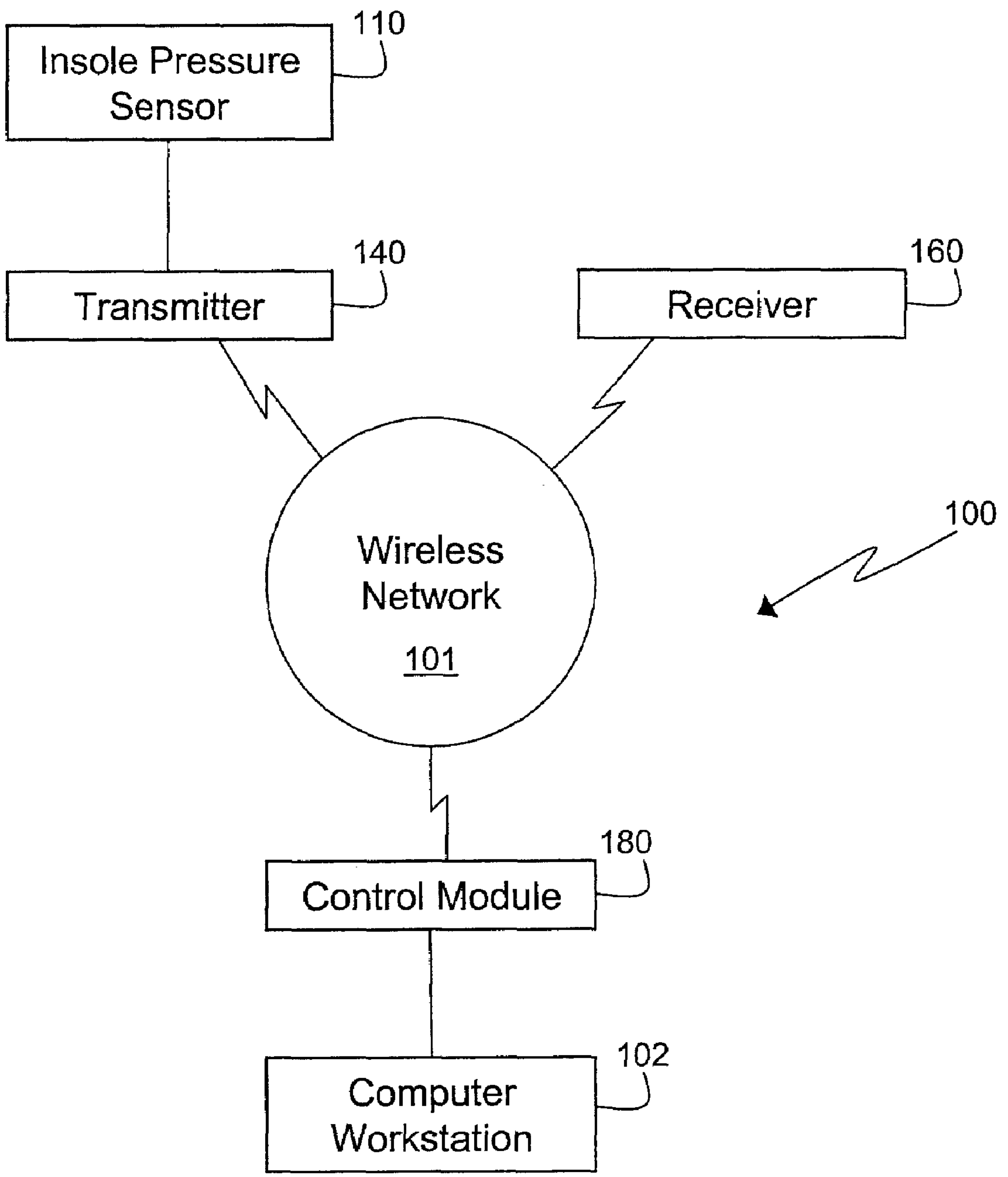
FIG. 1 is a block diagram of a system for use in gait assistive therapy, according to one aspect of the present invention.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms “a,” “an” and “the” include plural referents unless the context clearly dictates otherwise. Thus, for example, reference to an “oscillator” can include two or more such oscillators unless the context indicates otherwise.

Ranges may be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the end points of each of the ranges are significant both in relation to the other end point, and independently of the other end point.

As used herein, the terms “optional” or “optionally” mean that the subsequently described event or circumstance may or may not occur, and that the description includes instances where said event or circumstance occurs and instances where it does not.

In one embodiment, the gait assistive system of the present invention acts to provide an extra neural pathway for biofeedback to the subject and comprises an insole pressure sensor and means for communicating the position of at least a portion of a subject’s foot relative to the insole pressure sensor to the subject. For example and with reference to FIG. 1, the exemplary gait assistive system 100 comprises an insole pressure sensor 110, a transmitter 140, a wireless network 101, and a receiver 160. In one aspect, the insole pressure sensor is in communication with the transmitter, which may be in communication with the receiver via the wireless network. As may be appreciated, the transmitter may be in communication with the receiver via other means, such as wired communication.

Optionally, in one aspect, the system 100 also comprises a control module 180 and a computer work station in communication with the control module 102. The control module may be in communication with the transmitter 140 and receiver 160 via the wireless network 101 or via other means, such as, for example and not meant to be limiting, wired communication. Thus, the wireless network provides for multi-directional communication between each of the system components (e.g., the transmitter 140, receiver 160, and control module 102).

In one aspect, the wireless network 101 can be configured to transmit signals (e.g., an output signal generated by the transmitter being sent to the receiver) on multiple frequencies. This exemplary aspect can increase the chance of successful delivery by avoiding interference from other conflicting devices, whether they are similar devices using the same frequency band, unrelated devices using the same frequency band, or electronic products inadvertently producing noise on the same frequency band. In another aspect, the wireless network 101 can be configured to transmit signals multiple times to increase the chance that at least one signal will be successfully received. In various aspects, the system components (e.g., the transmitter 140, receiver 160, and control module 180) are configured to operate in a predetermined specific frequency band, such as, for example and not meant to be limiting, the 900 MHz radio frequency band).

Figure 2A:
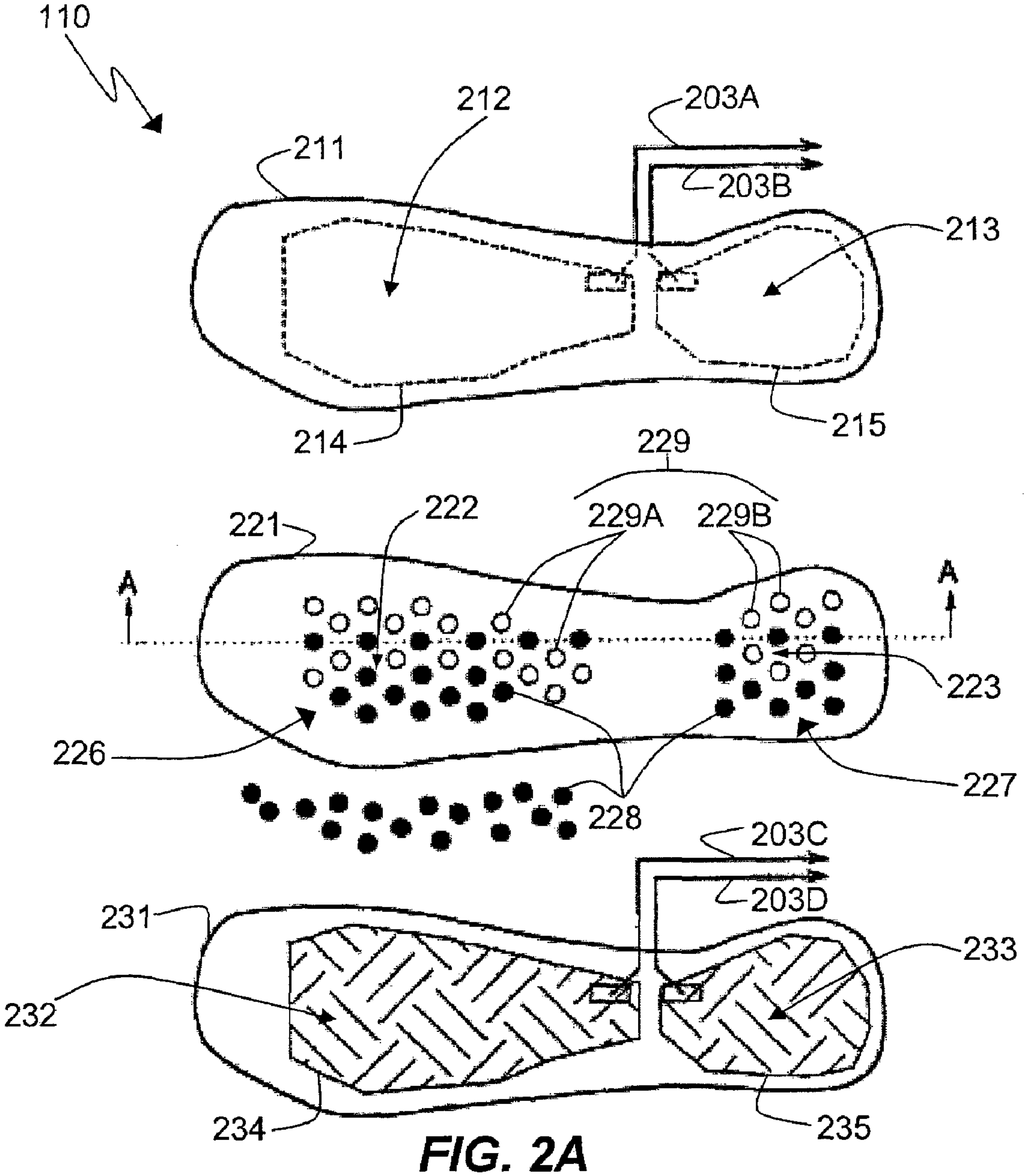
FIG. 2A is a schematic diagram illustrating an exemplary insole pressure sensor, according to one aspect of the present invention.

In one embodiment of the present invention, the insole pressure sensor 110 comprises a first portion, a second portion and a plurality of conductive foam cores. In one aspect, at least one of the foam cores is disposed within the first portion and at least another one of the foam cores is disposed within the second portion. For example and with reference to FIG. 2A, an insole pressure sensor 110 in one aspect of the present invention may be a layer 221 of material, such as foam, that has a first portion 226 and a second portion 227. In one aspect, the first portion corresponds to the ball portion 222 of a subject’s foot and the second portion corresponds to the heel portion 223 of a subject’s foot. As can be seen in FIG. 2A, each of the respective ball and heel portions of the insole pressure sensor defines a respective plurality of holes 229. In this aspect, a first plurality of holes 229A is positioned proximate the first portion (e.g., the ball portion) of the insole pressure sensor; and a second plurality of holes 229B is positioned proximate the second portion (e.g., the heel portion) of the insole pressure sensor. In one aspect, at least one of the plurality of foam cores 228 is disposed within one of the first plurality of holes and at least one of the plurality of foam cores is disposed within one of the second plurality of holes. In one aspect, the holes 229 may be arranged in a substantially grid-like pattern. Optionally, the holes can be arranged in a random pattern, or a combination of grid-like and random patterns.

In one aspect, the holes 229 are configured to retain the exemplary conductive foam cores 228. As such, the holes can have a diameter of about 1 mm to about 20 mm. In another aspect, the holes can have a diameter of between about 5 mm to about 15 mm, to include the additional exemplary diameters of 6, 7, 8, 9, 10, 11, 12, 13, and 14 mm. Likewise, the layer 221 of material is configured to provide some level of support to a subject’s foot, and therefore has at least a nominal thickness. In one aspect, the layer ranges from about 1 mm thick to about 25 mm thick. In another aspect, the layer ranges from about 2 mm thick to about 10 mm thick, to include the additional exemplary thicknesses of 3, 4, 5, 6, 7, 8, and 9 mm thick. It is contemplated that the layer 221 may comprise foam material that is adapted to provide support to a subject’s foot, while simultaneously absorbing shock of the foot’s pressure against the ground (or other walking surface).

In various aspects, the insole pressure sensor may comprise additional layers, such as, for example, a lower layer 231 and an upper layer 211. In this aspect, it is contemplated that the layer 221 described above would be positioned between the respective upper and lower layers and acts as a middle layer. The upper and lower layers, in one aspect, comprise a material that provides support to a subject’s foot, such as, for example and not meant to be limiting, foam and the like. As may be appreciated, each of the upper, middle and lower layers has an upper side and a lower side. Each of the layers in FIG. 2A is intended to be viewed from its upper side. As may also be appreciated, each of the upper and lower layers has a first portion and a second portion, similarly to the middle layer 221 as described above. In one aspect, the first portion of each layer corresponds to the ball portion of the respective layer and the second portion of each layer corresponds to the heel portion of the respective layer.

In one aspect, the upper layer has at least one upper conductive element 214 mounted to at least a portion of its lower side. In a further aspect, the upper layer 211 has a first upper conductive element 214 disposed or mounted proximate a ball portion 212 of the upper layer, and a second upper conductive element 215 disposed or mounted proximate a heel portion 213 of the upper layer. In one example, the conductive elements, in various aspects, including those described below, can comprise conductive fabric.

In another aspect and similar to the upper layer described above, the lower layer 231 in one aspect has at least one lower conductive element mounted to at least a portion of its upper side. For example, a first lower conductive element 234 is disposed or mounted proximate a ball portion 232 of the lower layer, and a second lower conductive element 235 is disposed or mounted proximate a heel portion 233 of the lower layer. Thus, in one aspect, at least a portion of one of the conductive elements is in communication with the first portion of the insole pressure sensor and at least a portion of one of the conductive elements is in communication with the second portion of the insole pressure sensor. As may be appreciated, the layers shown in FIG. 2 are exemplary, and are not necessarily drawn to scale. It is contemplated that the conductive elements may be larger or smaller than they appear in relation to the overall size of the respective layers on which they are disposed. Additionally, the layers are not necessarily formed in the orientation, i.e., for use in a left shoe of a subject, as shown in FIG. 2, and can be formed in any shape or orientation.

Figure 2B:
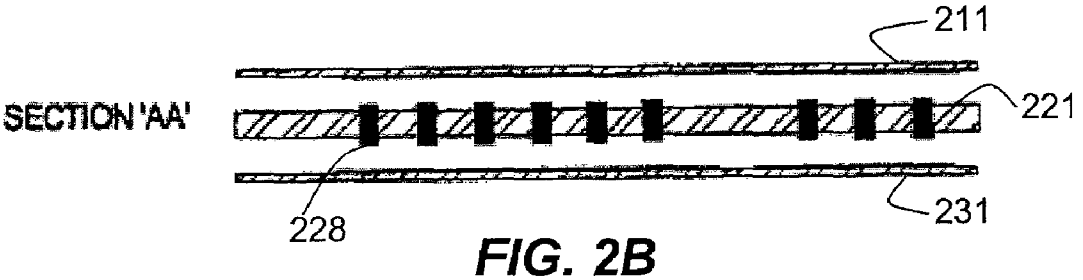
FIG. 2B is a cross-sectional view of the insole pressure sensor taken along line 'A-A' of FIG. 2A, according to one aspect of the present invention.

In one exemplary aspect, the lower layer 231 is mounted to the lower side of the middle layer 221, and the upper layer 211 is mounted to the upper side of the middle layer 221. Thus, in one aspect the insole pressure sensor can form a shoe insert. As described above, in one aspect each of the layers comprises foam material, and thus in one aspect the shoe insert is flexible. In another aspect, the respective upper and lower layers of foam have substantially the same shape, which can aid in aligning the layers prior to mounting them together. FIG. 2B illustrates a cross-section of section ‘A-A’ of an assembled insole pressure sensor. As can be seen, the insole pressure sensor 110 comprises an upper layer 211, a middle layer 221 which further comprises a plurality of foam cores 228 disposed within a plurality of holes, and a lower layer 231. These layers are shown as separated in FIG. 2B for illustration only. As may be appreciated, when the layers are mounted together as described above, at least a portion of the middle layer is in contact with at least a portion of each of the lower and upper layers. Thus, in one aspect, when the layers are mounted together, at least one conductive element is in communication with at least one conductive foam core.

As may be appreciated, the layers may be mounted by conventional mounting means, such as adhesion, for example and not meant to be limiting, glue, tape, or other adhesive products, riveting, stapling, or any other means or combination thereof for mounting surfaces together. In one aspect, the insole pressure sensor comprising multiple layers can be assembled and then trimmed to fit the shoe(s) of the respective subject. Optionally, the layers of the insole pressure sensor can be shaped and/or trimmed prior to mounting. Optionally, the insole pressure sensor can be inverted such that the upper layer is positioned on the bottom of the insole pressure sensor and the lower layer is positioned on the top of the insole pressure sensor so that it can be used in either the left or right shoe of the subject.

In various aspects, one or more electrical traces are provided and are in communication with one or more of the conductive elements, such as those described above. For example, a first electrical trace may be in communication with at least one of the conductive elements in communication with the first portion of the insole pressure sensor; likewise, a second electrical trace may be in communication with at least one of the conductive elements in communication with the second portion of the insole pressure sensor. For example and as shown in FIG. 2, one or more electrical traces may be in communication with the upper layer 211, such as the first electrical trace 203A in communication with the first upper conductive element 214 and the second electrical trace 203B in communication with the second upper conductive element 215. Alternatively, or in addition, one or more electrical traces may be in communication with the lower layer 231, such as the third electrical trace 203C in communication with the first lower conductive element 234 and the fourth electrical trace 203D in communication with the second lower conductive element 235. As described further below, the one or more electrical traces allow for communication between the insole pressure sensor and other components of the system. For example, in various aspects the electrical traces are in communication with one or more comparators, which are in communication with a transmitter.

Figure 3:
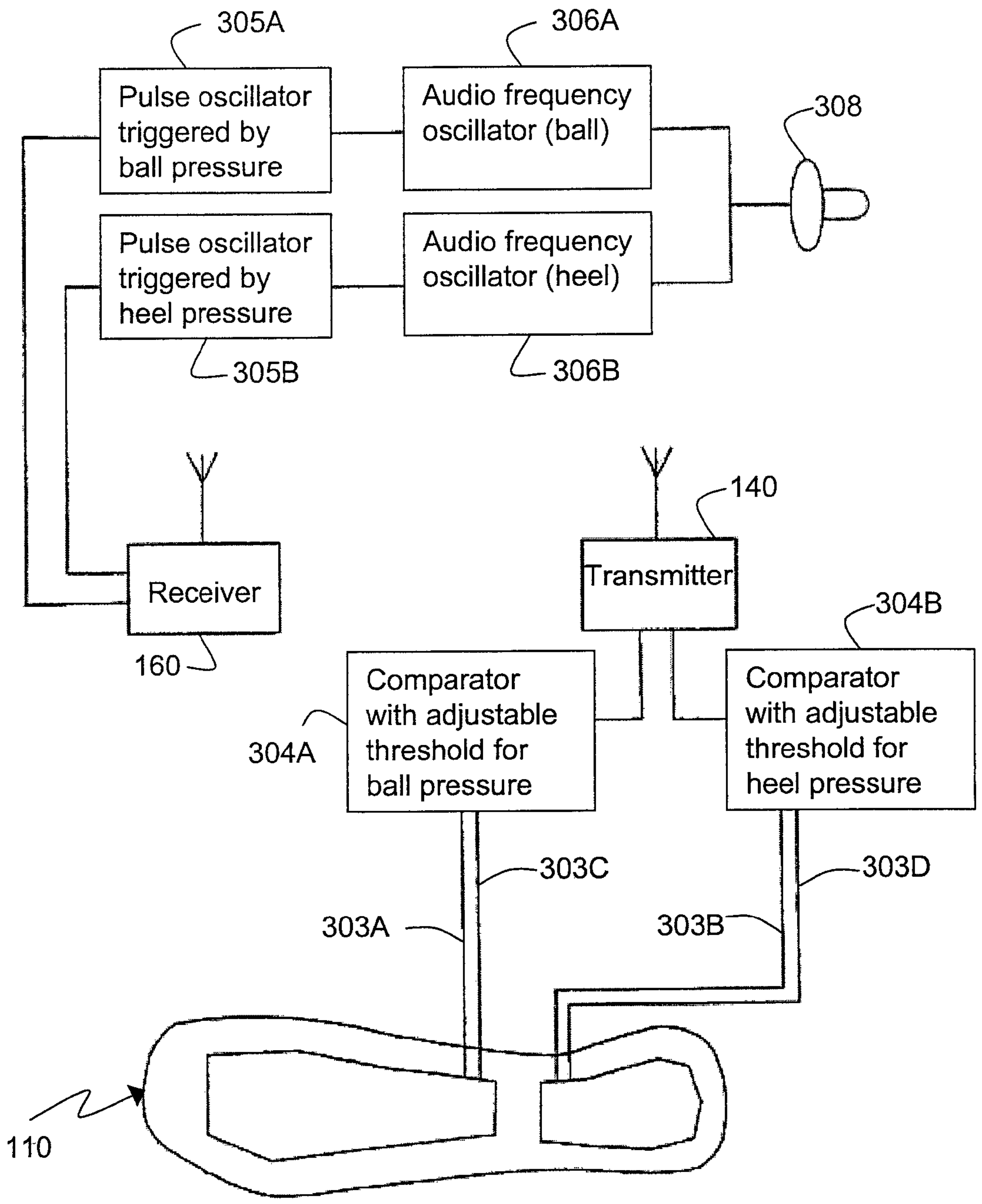
FIG. 3 is a schematic block diagram of an embodiment of the gait assistive system of the present invention, according to one aspect of the present invention in which an audible signal output is used.

Referring now to FIG. 3, an exemplary aspect of the system of the present invention is illustrated in which biofeedback information is provided audibly to a subject. In one aspect, an insole pressure sensor is in communication with one or more comparators via the one or more electrical traces. In an exemplary aspect, the respective first and second electrical traces (303A, 303C) are in communication with the ball portion of the insole pressure sensor 110. As may be appreciated, the first electrical trace 303A may be in communication with the upper conductive element proximate the ball portion of the upper layer, the second electrical trace 303C may be in communication with the lower conductive element proximate the ball portion of the lower layer, or vice versa. Likewise, in a further exemplary aspect, the respective third and fourth electrical traces (303B, 303D) are in communication with the heel portion of the insole pressure sensor.

In another aspect, the first and second electrical traces (303A, 303C) are in communication with a first comparator 304A, and the third and fourth electrical traces (303B, 303D) are in communication with a second comparator 304B. Each respective comparator is configured to generate an output signal when the pressure exerted by the subject on the respective ball or heel portion of the insole pressure sensor 110 exceeds a pre-set level. For example, the first comparator is configured to generate an output signal when pressure exerted on the ball portion of the insole pressure sensor exceeds a pre-set level and the second comparator is configured to generate an output signal when the pressure exerted on the heel portion of the insole pressure sensor exceeds a pre-set level. In one aspect, the pre-set level can be selectively set for each of the first and second portions of the insole pressure sensor. Thus, the pre-set levels for the respective first and second portions (for example, but not limited to, a ball and heel portion) may be the same or may differ. It is further contemplated that the pre-set levels for the respective ball and heel portions of the insole pressure sensor can be selectively set.

In some aspects, the system may additionally comprise an adjustable voltage divider network in communication with the comparator(s). The voltage divider network can be adjusted to prevent false signals which may arise from the normal pressure exerted by the foot on the insole pressure sensor, such as, for example, by the pressure of the shoe surrounding the subject's foot when not in contact with the ground or other walking surface.

The system, in one aspect, also comprises a transmitter 140 and receiver 160. The first and second comparators (304A, 304B) are in communication with transmitter. In one aspect, when the pressure in either or both portions of the insole pressure sensor exceeds a respective pre-set level, the respective comparator changes state and generates a digital output signal. The digital output signal is then encoded and communicated to the transmitter. In one aspect, the transmitter is located in the same enclosure as the comparator. Optionally, the transmitter may be located remotely from the comparator. In one aspect, the transmitter can be worn unobtrusively on the side of a subject's shoe, or on the subject's ankle.

In one aspect, the receiver 160 can be positioned remotely from the transmitter 140. Thus, in some aspects the transmitter can be in operable communication with the receiver by wireless communication. Optionally, the receiver can be positioned remotely from the transmitter, but the transmitter and receiver can be in wired communication. The output signal generated by the comparators is thus communicated to the receiver via the transmitter. In some aspects, the transmitter 140 and receiver 160 are addressable, thus ensuring exclusivity for the system. For example, in one aspect, a receiver is not initially paired with a corresponding transmitter. After the receiver is turned on, or otherwise activated, it 'listens' for wireless signals. Upon receipt of a signal from a transmitter, the receiver learns the serial number of the transmitter and stores the serial number in non-volatile memory and is "paired" with the transmitter. In this aspect, the receiver and transmitter are now paired with one another, and the receiver will only receive signals from the corresponding transmitter. One exemplary transceiver can be the Integration Associates IA4420 Universal ISM Band FSK Transceiver. In this exemplary device, both transmitter and receiver sections are integrated in a single chip. In one aspect, in the earpiece, only the receiver is used. In the transmitter and control station, both the transmitter and receiver sections can be used.

In one exemplary aspect, each output received by the receiver 160 is communicated to a pulse oscillator. For example, an output signal generated by the first comparator 304A, which is in communication with the ball portion of the insole pressure sensor 110 is communicated via the transmitter 140 and receiver 160 to a first pulse oscillator 305A. Likewise, an output signal generated by the second comparator 304B, which is in communication with the heel portion of the insole pressure sensor, is communicated via the transmitter and receiver to a second pulse oscillator 305B. The first pulse oscillator and second pulse oscillator are configured to provide a pulse, the length of which can be adjusted for each individual subject. In one aspect, such as shown in FIG. 3, each pulse generated by the pulse oscillators triggers a respective audio oscillator. For example, a pulse generated by the first pulse oscillator 305A triggers a first audio oscillator 306A. Likewise, a pulse generated by a second pulse oscillator 305B triggers a second audio oscillator 306B. Each respective audio oscillator is configured to generate a tone of a pre-set frequency and amplitude in response to the generated pulse signal from the respective pulse oscillator. In one aspect, the system comprises an earpiece 308 configured to transmit the generated tone to the subject. The tone generated by the first audio oscillator indicates that the pressure on a first portion (for example, but not limited to, the ball portion) of the insole pressure sensor exceeds the respective pre-set pressure threshold. Similarly, the tone generated by the second audio oscillator indicates that the pressure on a second portion (for example, but not limited to, the heel portion) of the insole pressure sensor exceeds the respective pressure threshold. Thus, in one aspect, the tones generated by the first and second audio oscillators differ. It is of course contemplated that the frequency, amplitude and the like of the tones can be adjusted to suit the individual subject. In one aspect, if pressures in both the ball and heel portions of the insole pressure sensor exceed respective pressure threshold levels, two tones will be generated. If two tones are generated, they may be transmitted to the subject consecutively, or in a specific order. For example, the heel tone (generated, for example, by the second audio oscillator 306B) may be transmitted first, followed by the ball tone (generated, for example, by the first audio oscillator 306A). Optionally, the ball tone may be transmitted prior to the heel tone. In another aspect, if a tone is actively being transmitted when a new output signal is received from the transmitter, the audio oscillator(s) will finish generating and transmitting the current tone before the next tone is sent.

In one aspect, the earpiece 308 may comprise one or more earpieces. For example, a subject using two insole pressure sensors may have two earpieces configured to transmit the signals of each insole pressure to the subject. In one aspect, a user may have an earpiece to be worn on the right-hand side of the head when using an insole pressure sensor in the right shoe. A user may have an earpiece to be worn on the left-hand side of the head when using an insole pressure sensor in the left shoe. In another aspect, a single earpiece may be used to transmit any number of audio signals to the subject. The earpiece may be a device worn inside at least a portion of the ear, such as commonly used hearing aid devices, ear buds, and the like. Optionally, the earpiece may be a device worn outside the ear, for example and not meant to be limiting, a bone anchored hearing aid and the like.

Figure 4:
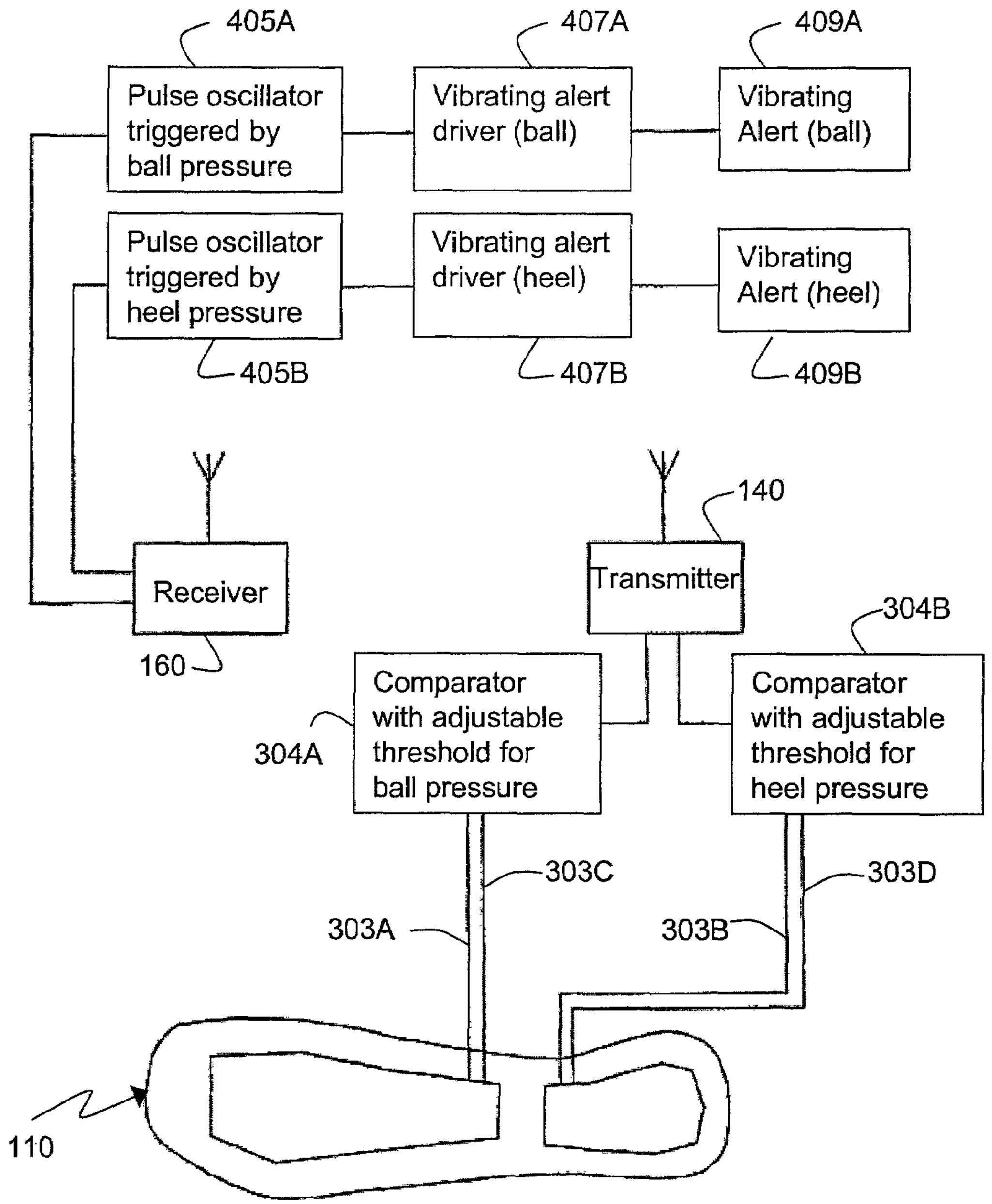
FIG. 4 is a schematic block diagram of an embodiment of the gait assistive system of the present invention, according to one aspect of the present invention in which a vibrating signal output is used.

In another exemplary aspect, the pulses generated by the first and second pulse oscillator are fed to a driver circuit to activate a vibrating alert. For example, FIG. 4 illustrates an exemplary system similar to that of FIG. 3. A first pulse oscillator 405A is configured to provide a pulse when it receives a signal from the first comparator 404A (via the transmitter 140 and receiver 160) indicating that pressure in a first portion (for example, but not limited to, the ball portion) of the insole pressure sensor exceeds a respective pre-set level. Likewise, a second pulse oscillator 405B is configured to provide a pulse when it receives a signal from the second comparator 404B (via the transmitter and receiver) indicating that pressure in a second portion (for example, but not limited to, the heel portion) of the insole pressure sensor exceeds a respective pre-set level. The pulse generated by the first pulse oscillator 405A is fed to a first vibrating alert driver 407A, which activates a first vibrating alert 409A. The pulse generated by the second pulse oscillator 405B is fed to a second vibrating alert driver 407B, which activates a second vibrating alert 409B. As may be appreciated, the first vibrating alert and second vibrating alert can be transmitted to the subject via a device capable of producing a vibrating signal, such as a mobile pager, a mobile telephone, or other device. A vibrating alert device can be worn on any part of the body to suit the subject.

Figure 5:
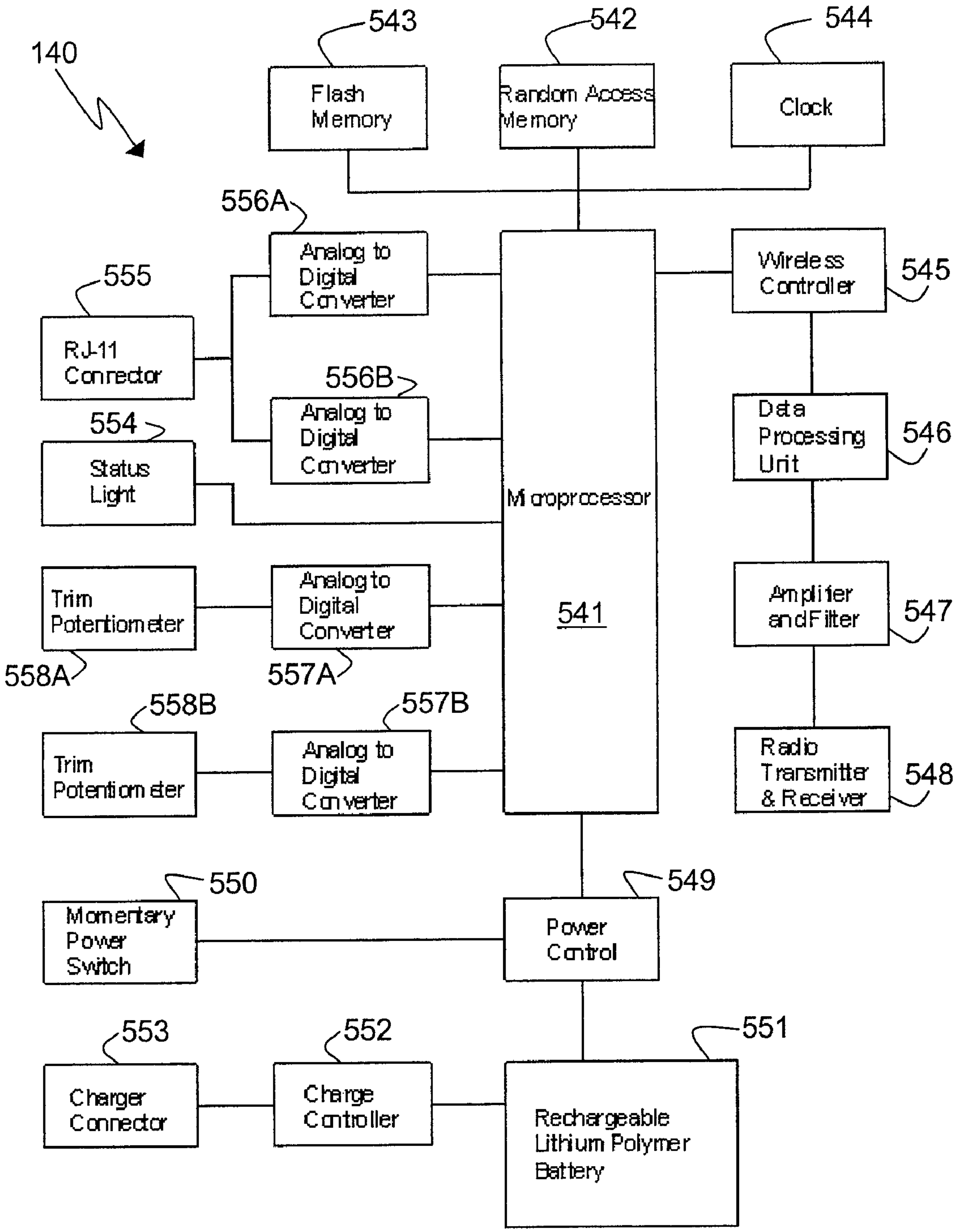
FIG. 5 is a schematic block diagram of a transmitter, according to one aspect of the present invention.

FIG. 5 illustrates one aspect of the transmitter 140 of the present invention. In one aspect, the transmitter is responsible for monitoring pressure in the various portions of the insole pressure sensor. In various aspects, the insole pressure sensor is an analog pressure sensor. The transmitter can convert the non-linear analog readings into weight measurements, such as, for example, pounds. When the pre-set pressure thresholds are exceeded, the transmitter is responsible for sending an output signal to the receiver, for example, via a wireless network. As may be appreciated, the elements of the transmitter 140 shown in FIG. 5 may be implemented as discrete electronics, integrated components, or a combination of both. In one aspect, the transmitter 540 comprises a connector, such as an exemplary RJ-11 connector 555 that provides an electrical interface with the insole pressure sensor. First and second analog to digital converters (556A, 556B) are connected to the RJ-11 connector and convert the non-linear analog readings from the insole pressure sensor, i.e., from the respective ball and heel portions, to digital values that are passed to the microprocessor. Third and fourth analog to digital converters (557A, 557B) are connected to respective trim potentiometers (e.g., first trim potentiometer 558A and second trim potentiometer 558B). In one aspect, the trim potentiometers are variable potentiometers configured as a resistor divider network and deliver a digital value to the microprocessor 541 based on the angle of rotation of the potentiometers. The digital values are used to control the pressure thresholds for the system. An exemplary trim potentiometer includes the Bourns 3362M-1-203, which has a 20K Ohm range. This exemplary potentiometer is configured so that a screwdriver can be used to set the value.

In a further aspect, the microprocessor 541 executes the logic functions of the transmitter 140. For example, in one aspect the microprocessor evaluates the digital inputs received from the first and second analog to digital converters 556A, 556B, i.e., the inputs received from the insole pressure sensor. The microprocessor also evaluates the digital inputs received from the third and fourth analog to digital converters 557A, 557B, i.e., the inputs received from the first and second trim potentiometers 558A, 558B. In other aspects, the microprocessor is configured to send and receive wireless messages. The transmitter 140 also comprises memory in communication with the microprocessor 541. The memory can comprise non-volatile memory, such as read-only memory (ROM), erasable programmable read-only memory (EPROM), electrically erasable programmable read-only memory (EEPROM), or flash memory 543. The non-volatile memory may be used, for example, to store data such as the pre-set pressure threshold for the various portions of the insole pressure sensor. The memory may also comprise volatile memory, such as random access memory (RAM) 542. A clock may also be provided 544 to allow the microprocessor to measure elapsed time.

The transmitter 140 also comprises a wireless controller 545, data processing unit 546, amplifier and filter 547, and radio transmitter and receiver 548. The wireless controller 545 is configured to provide wireless configuration, transmission and reception functions to the microprocessor. The data processing unit encodes digital data into wireless transmissions and decodes digital data from wireless receptions. The amplifier and filter are configured to filter signals in a selected operating frequency and amplifies those signals upon reception. On transmission, the amplifier and filter place the signal onto the base band frequency. The radio transmitter and receiver drive the transmission signal into an antenna of the transmitter and capture signals received by the transmitter.

As may be appreciated, the transmitter 140 may be powered in various ways. In one aspect, a rechargeable lithium polymer battery 551 is provided to power the transmitter during operation. A power control 549 may be provided to allow the microprocessor 541 to monitor battery voltage and allow the microprocessor to shut off power to the transmitter due to a low battery voltage or inactivity timeout. In one aspect, the power control can be a solid state, electronically controlled momentary switch. In this example, when power is applied to its control line, the momentary switch closes and delivers battery power to the entire circuit. In one example, the momentary switch can connect battery power through a diode to the control line of the electronic switch while the switch is being depressed. In addition, the microprocessor can have an output signal line that is attached to the control line of the electronic switch and an input signal line attached to the momentary switch, for example, upstream of the diode. In operation, in one exemplary aspect, when power is applied to the microprocessor, which occurs when the momentary switch is depressed, the microprocessor immediately drives an output signal to the control line of the electronic switch. When the momentary switch is released, the microprocessor is configured to keep the electronic switch closed by continuing to drive the control line. Thus, during operation, the microprocessor can monitor the momentary power switch through its input signal line. When the microprocessor determines that the momentary switch has been depressed for a predetermined period of time, it then waits for the switch to be released. Finally, when the microprocessor shuts off its output signal, which opens the electronic switch and shuts down the circuit. As one skilled in the art will appreciate, the microprocessor, through conventional software algorithms, can also be configured to make other functional decisions based on the length of time the momentary switch is depressed.

A charge connector 553 and charge controller 552 may be provided to allow a DC power source to be attached to the transmitter for recharging the battery. The charge controller 552 ensures that proper voltages and currents are provided to the battery 551 for recharging. A status light 554, such as, for example and without limitation, a light emitting diode, or "LED", may be provided as part of the transmitter to provide visual status signals to the subject.

Figure 6:
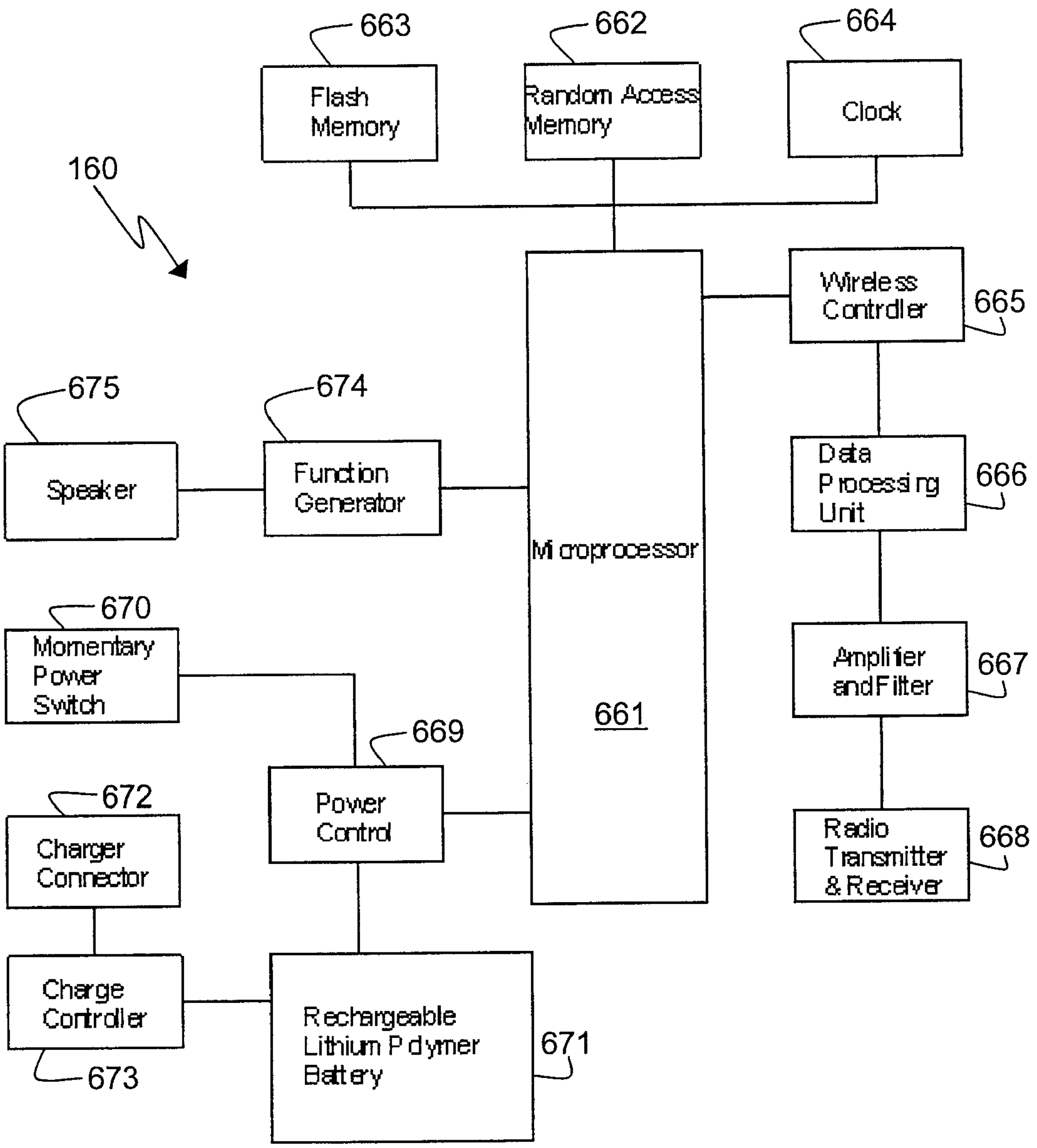
FIG. 6 is a schematic block diagram of a receiver, according to another aspect of the present invention.

FIG. 6 illustrates an exemplary receiver 160 according to one aspect of the present invention. In one aspect, the receiver is responsible for receiving output signals from the transmitter 140 and deliver sensory signals, such as the previously described audible tones or vibratory alerts, to the subject. As may be appreciated, the elements of the receiver shown in FIG. 6 may be implemented as discrete electronics, integrated components, or a combination of both. Similarly as described above with respect to the transmitter, the receiver comprises a microprocessor 661 configured to execute the logic functions of the receiver 660, memory (such as flash memory 663 and RAM 662), and a clock 664 for allowing the microprocessor to measure elapsed time. The receiver also comprises a rechargeable lithium polymer battery 671 (that may be recharged via the charger connector 672 and charge controller 673), and a power control 669 that allows the microprocessor 661 to monitor battery voltage and shut off power to the receiver due to low battery voltage or inactivity timeout.

In one aspect, the receiver 160 comprises means for transmitting an audible tone to the subject. For example, in one aspect the receiver comprises a function generator 674 that allows various fixed frequencies in the audible range to be programmed to drive the speaker 675. The receiver also comprises a wireless controller 665, data processing unit 666, amplifier and filter 667, and radio transmitter and receiver 668. The wireless controller is configured to provide wireless configuration, transmission, and reception functions to the microprocessor. The data processing unit encodes digital data into wireless transmissions and decodes digital data from the wireless receptions. The amplifier and filter are configured for filtering signals in a selected operating frequency and amplifies those signals upon reception. The radio transmitter and receiver are configured to drive the transmission signal into an antenna of the receiver and to capture signals received by the antenna.

In a further aspect, the system 100 of the present invention also comprises a control module 180, as illustrated in FIG. 1. The control module is configured to receive the output signal generated by the transmitter 140 connected to the insole pressure sensor 110. The control module can be operated by a user at a remote computer work station 102. The user may be, for example, a physical therapist, doctor, other medical professional, or another user. In one aspect, the control module comprises means for monitoring the pressure exerted on one or more portions of the insole pressure sensor via the output signal generated by the transmitter.

Figure 7:
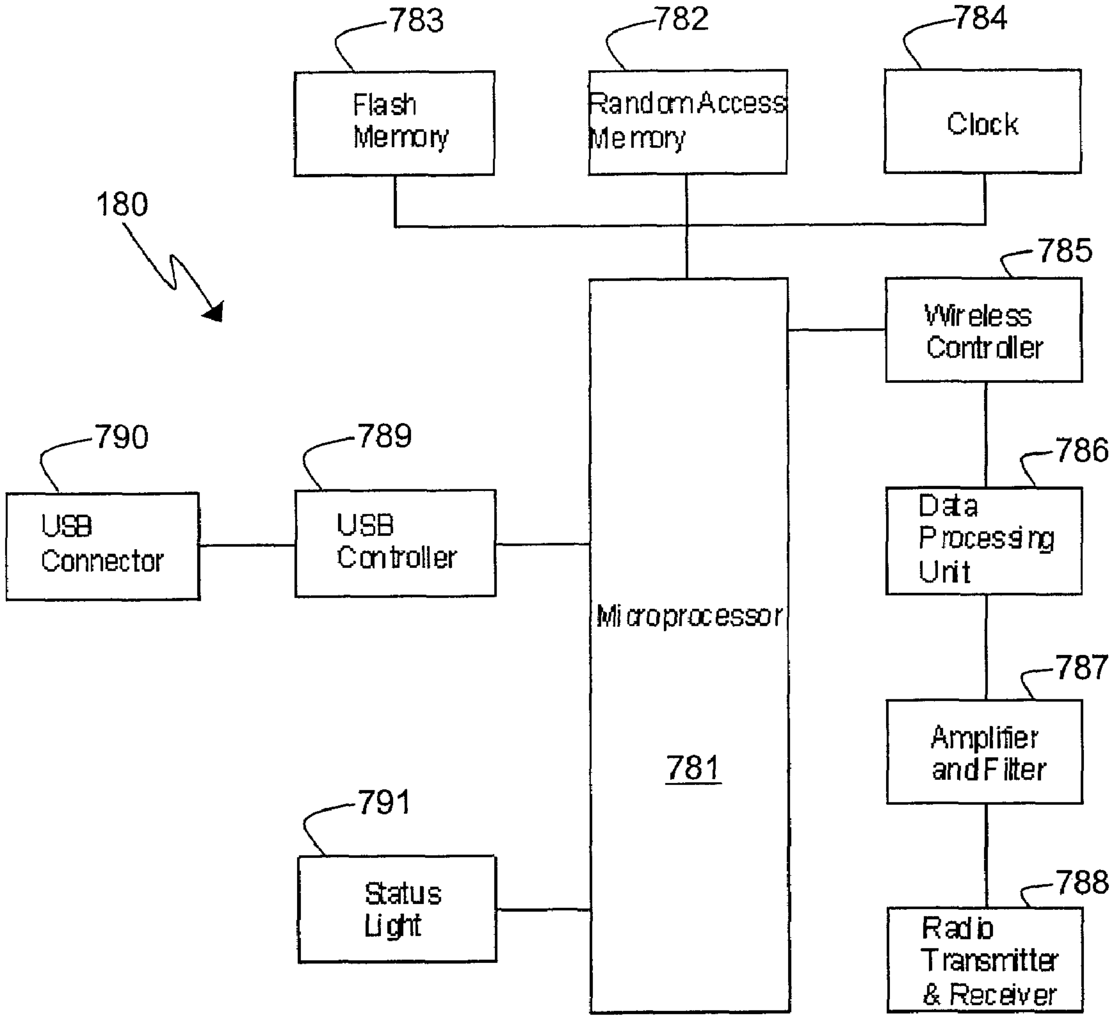
FIG. 7 is a schematic block diagram of a control module, according to yet another aspect of the present invention.

FIG. 7 illustrates an exemplary aspect of the control module 180 of the present invention. Several elements of the control module are similar to those described above with respect to the receiver 160 and transmitter 140. For example, the control module 780 comprises a microprocessor 781, memory (such as flash memory 783 and RAM 782), a clock 784, wireless controller 785, data processing unit 786, amplifier and filter 787, and radio transmitter and receiver 788. In one aspect, the control module 180 serves as a second receiver and receives output signals generated by the transmitter. The control module also comprises a USB (Universal Serial Bus) connector 790 that provides a communication pathway between the control module and a computer work station. A USB controller 789 provides serial data communications to and from the control module using the USB industry standard.

In one aspect, the computer work station 102 as illustrated in FIG. 1 is in communication with the control module 180. As discussed above, the computer work station and control module may be in communication via a USB connector or any other connection means, such as, without limitation, a serial connector, wireless communications, and the like. In one aspect, the computer work station provides an operating environment comprising a graphical user interface (GUI), input devices (such as a keyboard, mouse, trackball, and the like), output devices (such as a monitor and the like), a means for connecting to the control module, and a software operating environment.

The software operating environment, in one aspect, executes a USB device driver and software for use by a user, such as a physical therapist. In one aspect, the software allows a user to monitor the pressure being applied by the subject to the insole pressure sensor (e.g., the ball and heel portion of the insole pressure sensor). In another aspect, the software is configured to provide information (e.g., system parameters, pressure sensor measurements, etc.) to the user, and receive input from the user. This input, in one aspect, comprises a pre-set pressure threshold level for various portions of the insole pressure sensor (for example, but not limited to, the ball and heel portions).

In one aspect, the present invention provides a method of providing biofeedback information to a subject for gait assistive therapy. In one aspect, this comprises monitoring pressure applied by the subject to a respective ball and heel portion of an insole pressure sensor, monitoring a pressure threshold for the respective ball and heel portions of the insole pressure sensor, and transmitting an output signal when the pressure in one or both of the ball and heel portions exceeds a pre-determined pressure threshold. In one aspect, the method may be implemented through use of a system as described herein.

In an additional aspect, monitoring the pressure threshold for the ball and heel portions of the insole pressure sensor comprises determining a normative pressure exerted by a ball and heel portion of a foot of the subject and using the normative pressure to set the pre-determined pressure thresholds for each of the respective ball and heel portions of the insole pressure sensor. In one aspect, the normative pressure may be determined by placing the insole pressure sensor in an uninjured or unaffected foot of the subject to determine the amount of pressure that the subject's foot ordinarily exerts during normal gait movement. In another aspect, the normative pressure may be determined using scientific data that provides, for example, a normative pressure that is exerted by persons having similar weight, height, and other physical features as the subject. In other aspects, the normative pressure used to set the pre-determined pressure thresholds may be determined by other means.

Transmitting an output signal, in one aspect, comprises transmitting an audible signal. The signal may be transmitted when, for example, pressure in one or more portions of an insole pressure exceeds a respective pre-determined threshold. For example, if pressure in the ball portion of the insole pressure sensor exceeds its pre-determined pressure threshold level, an audible signal is transmitted to the subject. If pressure in the heel portion of the insole pressure sensor exceeds its pre-determined pressure threshold level, an audible signal is likewise transmitted to the subject. In one aspect, the signal generated by the transmitter in response to excessive pressure in the ball portion is different from the signal generated by the transmitter in response to excessive pressure in the heel portion of the insole pressure sensor. Thus, in one aspect, the audible signal signaling excessive pressure in the ball portion differs from the audible signal signaling excessive pressure in the heel portion of the insole pressure sensor. The audible signals may differ, for example, in amplitude and frequency, thus emitting different tones to the subject.

In one aspect, the generated output signal is transmitted via a wireless signal to a receiver. The receiver may be located remotely from the transmitter and transmits an audible signal to the subject. In one aspect, the receiver is an earpiece. In other aspects, the transmitted output signal may be transmitted wirelessly to a receiver configured to generate a different type of signal, such as an exemplary vibrating signal, to the subject. The receiver may be part of, or in communication with a device configured to transmit such a signal, such as a mobile pager or mobile telephone.

Optionally, the output signal is transmitted wirelessly to a control station, and pressures exerted on the ball and heel portion of the insole pressure sensor by the respective ball and heel portion of the subject's foot are monitored at the control station. Thus, in one aspect, the control station serves as a second receiver. As described above, the control station may be associated with a physical therapist, doctor, other medical professional, or other user. The user may use the control station to set a pre-determined pressure threshold for the respective ball and heel portion.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for providing biofeedback information to a subject for gait assistive therapy, comprising:

an insole pressure sensor comprising:

a first portion;

a second portion;

a plurality of conductive foam cores;

a lower layer of foam having an upper side;

at least one bottom conductive element mounted to at least a portion of the upper side of the lower layer of foam;

a middle layer of foam defining at least one plurality of holes, the at least one plurality of holes comprising a first plurality of holes that are positioned proximate the first portion and a second plurality of holes that are positioned proximate the second portion, wherein at least one of the plurality of conductive foam cores is disposed within at least one of the first plurality of holes and wherein at least one of the plurality of conductive foam cores is disposed within at least one of the second plurality of holes;

an upper layer of foam having a lower side; and at least one upper conductive element mounted to at least a portion of the lower side of the upper layer of foam; and means for communicating the position of at least a portion of the subject's foot relative to at least one of the plurality of conductive foam cores to the subject.

2. The system of claim 1, wherein the first portion is a heel portion, and the second portion is a ball portion.

3. The system of claim 1, wherein at least a portion of one of the conductive elements is in communication with the first portion of the insole pressure sensor and at least a portion of one of the conductive elements is in communication with the second portion of the insole pressure sensor.

4. The system of claim 3, wherein the lower layer of foam is mounted to a lower side of the middle layer of foam and the upper layer of foam is mounted to an upper side of the middle layer of foam.

5. The system of claim 4, wherein the insole pressure sensor forms a substantially flexible shoe insert.

6. The system of claim 4, wherein the bottom conductive element and the upper conductive element comprise conductive fabric.

7. The system of claim 4, wherein the upper and lower layers of foam have substantially the same shape.

8. The system of claim 4, wherein the means for communicating comprises:

a plurality of electrical traces, wherein a first electrical trace of the plurality of electrical traces is in communication with at least one of the conductive elements in communication with the first portion, and wherein a second electrical trace of the plurality of electrical traces is in communication with at least one of the conductive elements in communication with the second portion; and a pair of comparators, wherein the pair of comparators are in communication with the plurality of electrical traces, one comparator of the pair of comparators being in communication with the first electrical trace and the other comparator of the pair of comparators being in communication with the second electrical trace, and wherein each of the comparators of the pair of comparators are configured to generate an output signal when the pressure exerted by the subject on the respective first or second portion of the insole pressure sensor exceeds a pre-set level.

9. The system of claim 8, wherein the pre-set level can be selectively set for the first and second portions of the insole pressure sensor.

10. The system of claim 8, further comprising:

a transmitter; and a receiver, wherein the receiver is positioned remotely from the transmitter, and wherein the pair of comparators is in communication with the transmitter such that the generated output signal is communicated to the receiver.

11. The system of claim 10, further comprising:

a control module in communication with the transmitter and configured to receive the generated output signal, comprising means for monitoring the pressure exerted on at least a portion of the insole pressure sensor.

12. The system of claim 10, further comprising a first pulse oscillator and a second pulse oscillator in communication with the receiver, wherein the first pulse oscillator generates a pulse signal in response to the received output signal when the comparator senses pressure in the first portion of the insole pressure sensor and wherein the second pulse oscillator generates a pulse signal in response to the received output signal when the comparator senses pressure in the second portion of the insole pressure sensor.

13. The system of claim 12, further comprising a first audio oscillator and a second audio oscillator, wherein the first audio oscillator is in communication with the first pulse oscillator and the second audio oscillator is in communication with the second pulse oscillator, and wherein each respective audio oscillator is configured to generate a tone of a pre-set frequency and amplitude in response to the generated pulse signal from the respective pulse oscillator.

14. The system of claim 13, wherein the pre-set frequency and amplitude of the tone generated by the first audio oscillator indicates that pressure on the first portion of the insole pressure sensor exceeds the pre-set level, and the pre-set frequency and amplitude of the tone generated by the second audio oscillator indicates that pressure on the second portion of the insole pressure sensor exceeds the pre-set level.

15. The system of claim 13, wherein the generated tones of the respective first and second audio oscillators differ.

16. The system of claim 13, further comprising an earpiece configured to transmit the generated tone to the subject.

17. A method of providing biofeedback information to a subject for gait assistive therapy, comprising:

providing an insole pressure sensor comprising:

a ball portion;

a heel portion;

a lower layer of foam having an upper side;

at least one bottom conductive element mounted to at least a portion of the upper side of the lower layer of foam;

a middle layer of foam defining at least one plurality of holes, the at least one plurality of holes comprising a first plurality of holes that are positioned proximate the ball portion and a second plurality of holes that are positioned proximate the heel portion, wherein at least one of the plurality of conductive foam cores is disposed within at least one of the first plurality of holes and wherein at least one of the plurality of conductive foam cores is disposed within at least one of the second plurality of holes;

an upper layer of foam having a lower side; and at least one upper conductive element mounted to at least a portion of the lower side of the upper layer of foam;

monitoring pressure applied by the subject to the ball and heel portion of the insole pressure sensor;

monitoring a pressure threshold for each of the ball and heel portions of the insole pressure sensor; and transmitting an output signal when the pressure in at least one of the ball and heel portion of the insole pressure sensor exceeds a pre-determined pressure threshold.

18. The method of claim 17, wherein the step of monitoring the pressure threshold comprises:

determining a normative pressure exerted by a ball and heel portion of a foot of the subject; and using the normative pressure to set the pre-determined pressure thresholds for each of the ball and heel portions of the insole pressure sensor.

19. The method of claim 17, wherein transmitting an output signal comprises transmitting an audible signal when the pressure in at least one of the ball and heel portions of the insole pressure sensor exceeds the respective pre-determined pressure threshold.

20. The method of claim 17, wherein transmitting an output signal comprises transmitting a wireless signal to a receiver.

21. The method of claim 20, wherein the receiver is an earpiece.

22. The method of claim 17, wherein transmitting an output signal comprises:

transmitting a first output signal when pressure in the ball portion of the insole pressure sensor exceeds its respective pre-determined pressure threshold; and transmitting a second output signal when pressure in the ball portion of the insole pressure sensor exceeds its respective pre-determined pressure threshold;

wherein the first output signal and second output signal differ.

23. The method of claim 22, wherein the first output signal and second output signal are audible tones.

24. The method of claim 17, wherein transmitting an output signal comprises:

transmitting a wireless signal to a control station; and monitoring the pressure exerted on the ball and heel portion of the insole pressure sensor by the respective ball and heel portion of the subject's foot at the control station.

* * * * *